United States Patent [19]

Aoshima et al.

[11] 4,236,034
[45] Nov. 25, 1980

[54] PROCESS FOR PRODUCING TERT-BUTANOL FROM MIXED BUTYLENES

[75] Inventors: Atsushi Aoshima, Yokohama; Toshiaki Murobushi; Ryoichi Mitsui, both of Fuji; Nobuhiro Tamura, Chigasaki, all of Japan

[73] Assignee: Asahi Kasei Kogyo Kabushiki Kaisha, Osaka, Japan

[21] Appl. No.: 46,315

[22] Filed: Jun. 7, 1979

[30] Foreign Application Priority Data

Aug. 6, 1978 [JP] Japan .................... 53/683267
Oct. 31, 1978 [JP] Japan .................... 53/133237

[51] Int. Cl.³ .................................... C07C 29/04
[52] U.S. Cl. .................................... 508/898; 568/895; 568/897; 568/899; 568/900; 568/901
[58] Field of Search ............ 568/898, 899, 900, 901, 568/895, 896, 897

[56] References Cited

U.S. PATENT DOCUMENTS

| 2,070,258 | 2/1937 | Coleman et al. | 568/899 |
| 2,162,913 | 6/1939 | Eversole et al. | 568/898 |
| 3,644,497 | 2/1972 | Mesich | 260/410.9 R |
| 3,758,615 | 9/1973 | Izumi et al. | 568/901 |
| 4,180,688 | 12/1979 | Imsizumi et al. | 568/898 |

FOREIGN PATENT DOCUMENTS

| 931166 | 7/1973 | Canada . |
| 50-35052 | 11/1975 | Japan . |
| 50-35053 | 11/1975 | Japan . |
| 51-13711 | 2/1976 | Japan . |
| 487384 | 6/1938 | United Kingdom . |
| 1281120 | 7/1972 | United Kingdom . |

Primary Examiner—Joseph E. Evans

[57] ABSTRACT

A process for producing tert-butanol by selective hydration of isobutylene in a hydrocarbon mixture comprising isobutylene and n-butene where an aqueous solution is used which contains a heteropolyacid, characterized in that the hydration reaction of isobutylene is carried out at a temperature of less than 100° C.

24 Claims, 3 Drawing Figures

○ CONCENTRATION OF TERT-BUTANOL = $\frac{\text{TERT-BUTANOL}}{\text{WATER+TERT-BUTANOL}} \times 100$

□ RATIO OF SEC-BUTANOL TO TERT-BUTANOL

△ RATIO OF DIISOBUTYLENE TO TERT-BUTANOL

○ CONCENTRATION OF TERT—BUTANOL = $\dfrac{\text{TERT-BUTANOL}}{\text{WATER+TERT-BUTANOL}} \times 100$

□ RATIO OF SEC—BUTANOL TO TERT—BUTANOL

△ RATIO OF DIISOBUTYLENE TO TERT—BUTANOL

PROCESS FOR PRODUCING TERT-BUTANOL FROM MIXED BUTYLENES

BACKGROUND OF THE INVENTION

1. Field of the Invention

This invention relates to a process for producing tert-butanol by selective hydration of isobutylene in a hydrocarbon mixture comprising isobutylene and n-butene.

2. Description of the Prior Art

Tert-butanol is useful as an industrial starting material for preparing a variety of products. For example, tert-butanol is employed as a starting material for preparing methacrylonitrile or methacrolein which is an intermediate for preparing methyl methacrylate, and methacrylonitrile or methacrolein cannot be obtained from sec-butanol originating from the hydration of n-butene.

Heretofore, in selectively hydrating the isobutylene in a mixture of isobutylene and n-butene, a 50 to 65% sulfuric acid or hydrochloric acid, a hydrochloric acid solution of a metal chloride, a strongly acidic ion-exchange resin or a solid acid is employed as the catalyst. However, according to the method of using sulfuric acid, the dimer, trimer and polymers of isobutylene are by-produced and part of n-butene, especially 1-butene tends to be hydrated to give sec-butanol, and furthermore, the strong corrosion of sulfuric acid requires expensive corrosion-resistant materials, making an industrial plant uneconomical. The method of using an inorganic acid such as hydrochloric acid or a halide such as tin chloride disadvantageously by-produces tert-butyl halides and also has the problem of the material of the plant due to their remarkable corrosion.

In order to avoid these disadvantages there is provided a method of using a strongly acidic ion-exchange resin or an insoluble solid acid, but their hydration activity is low and generally a high hydration temperature ranging from 120° C. to 200° C. is required. Moreover, at this temperature the life of the ion-exchange resin is short and filtration of finely pulverized particles from a fluidized liquid is very difficult and as a result, the proces becomes complicated. Fundamentally, with increased temperatures the conversion of isobutylene to tert-butanol decreases more from the standpoint of chemical equilibrium. Accordingly, the concentration of tert-butanol in an aqueous solution at equilibrium becomes low when the catalyst requiring high temperatures is used. As a result, the reaction apparatus unfavorably becomes large from the industrial viewpoint.

Generally, it is known that an aqueous solution of a heteropolyacid such as tungstosilicic acid, molybdophosphoric acid and tungstophosphoric acid can be employed in hydrating olefins. However, as far as an olefin mixture of n-butylene and isobutylene is concerned, there has not been known such a catalyst having a high activity even under mild reaction conditions that can selectively convert isobutylene into tert-butanol without forming polymers such as the dimer and the trimer of isobutylene and with n-butenes unreacted while maintaining the initial catalytic activity for a long period of time and that makes possible use of an ordinary industrial material, for example, stainless steel as the construction material.

More specifically, British Pat. No. 1,281,120, Japanese Patent Publication Nos. 35052/1975 and 35053/1975 describe the hydroxylation of a 1:1 mixture of isobutylene and n-butene in the presence of a heteropoly-acid ion. With taking into account the drawbacks of corrosion of the material of the reactor and the side reactions, the hydration is conducted at a high temperature and a high pressure (200° C., 250 Kg/cm$^2$) while maintaining the concentration of the heteropoly-acid low and the pH of the reaction high, resulting in a 1:1 mixture of sec-butanol and tert-butanol as the product. In this case, in order to complete the reaction, several hours are necessary due to the low catalytic activity. Moreover, the selective hydration of isobutylene to tert-butanol in the presence of n-butene cannot be achieved.

Further, Japanese Patent Application (OPI) No. 13711/1976 discloses that when the hydration of isobutylene is conducted at a concentration of the heteropoly-acid as high as 10 to 70% by weight at a temperature of from 100° C. to 170° C., corrosion of the material of reactors and by-production of olefin polymers can be prevented and the life and the hydration activity of the catalyst are satisfactory. However, there is no disclosure on the selective hydration of isobutylene in mixed butylenes.

Also, in the reaction system using the conventional catalysts, the tert-butanol produced is substantially present in the aqueous liquid phase, and accordingly, after the removal of the remaining hydrocarbon mixture, for example, by separation of the organic liquid phase from the aqueous liquid phase, tert-butanol is recovered from the aqueous liquid phase by any conventional method such as distillation under reduced pressure and salting-out.

However, in recovering tert-butanol from the aqueous liquid phase by distillation, polymers are produced and a large quantity of heat is necessary. The distillate contains more water than the azeotropic mixture of water and tert-butanol and in general, it is impossible to increase the concentration of tert-butanol from a range of 80% to 89%. In the salting-out method, removal of the salt is necessary for re-using the acid catalyst contained but this is very difficult and industrially impractical.

Japanese Patent Application No. 4165/1972 discloses a process for hydrating isobutylene in the presence of an acid catalyst and an inorganic acid salt in order to make the tert-butanol produced the upper phase. However, this method employs sulfuric acid as the catalyst and the hydrocarbons such as n-butene are not liquefied. As a result, the tert-butanol produced contains a large amount of water as clearly understood from the Example of this prior art and cannot be obtained at a high concentration. Further, the presence of sulfuric acid causes strong corrosion of the material of the reactor and a large amount of diisobutylene is by-produced and thus, this method is industrially of little value.

SUMMARY OF THE INVENTION

Accordingly, the present invention in one embodiment provides a process for producing tert-butanol which comprises contacting a hydrocarbon mixture comprising isobutylene and n-butene with an aqueous solution containing a heteropoly-acid having at lest one condensation coordinate atom selected from the group consisting of Mo, W and V at a temperature of less than 100° C. to effect the selective hydration reaction of isobutylene.

The present invention in another embodiment provides a process for producing tert-butanol as described above which includes separating the remaining hydrocarbons from the resulting hydration reaction mixture liquid at a temperture of at most about 70° C. and recovering or purifying tert-butanol at a temperature of at most about 70° C.

In a further embodiment, the invention provides a process for producing tert-butanol as described above, wherein the selective hydration reaction of isobutylene is conducted at an amount of tert-butanol in the aqueous liquid phase in the range of from about 5 to about 30% by weight based on the total amount of the aqueous liquid phase.

DETAILED DESCRIPTION OF THE INVENTION

Figure 1:
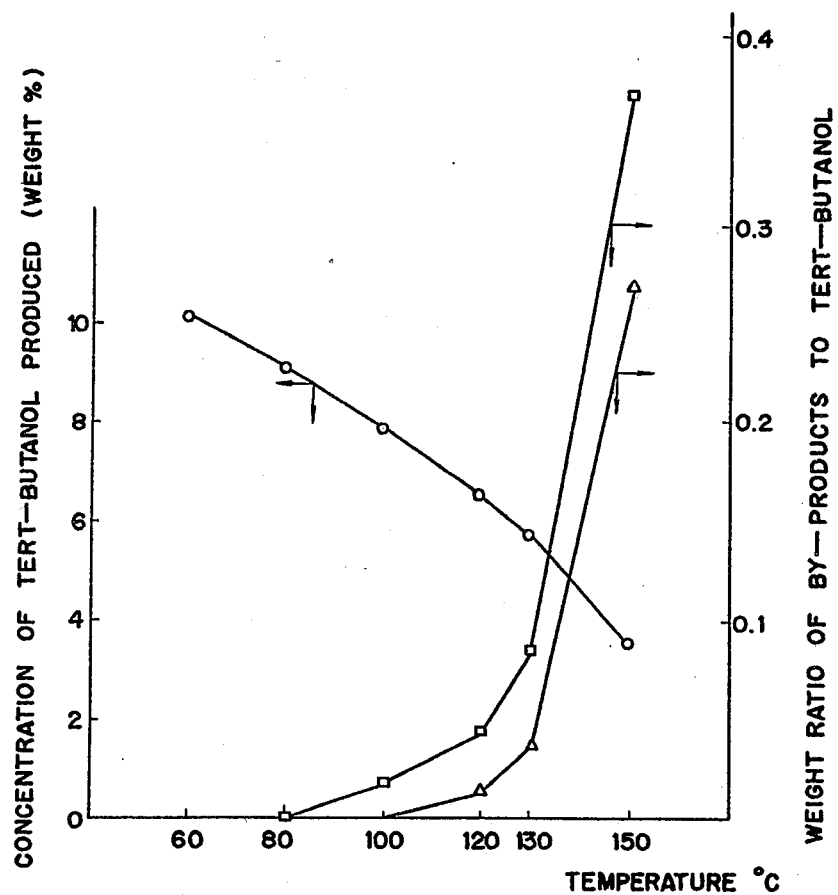
FIG. 1 illustrates the results of Example 2 of this invention.

Suitable hydrocarbon mixtures containing isobutylene and n-butene which may be employed in this invention include any mixtures of isobutylene and n-butene which may additionally contain cis-2-butene, trans-2-butene, a saturated hydrocarbon such as propane, a butane, a pentane or an aromatic hydrocarbon; $C_4$ distillates by-produced from a fluidized catalytic cracking apparatus for petroleum; distillates of catalytic dehydrogenation of n-butene; and so-called spent B-B fractions containing, as the main components, isobutylene and n-butenes obtained by removal of a most part of butadiene from an $C_4$ fraction in cracking naphtha.

The heteropoly-acid which can be employed as the catalyst in this invention has at least one condensation coordinate atom selected from the group consisting of Mo, W and V and may additionally has other condensation coordinate atoms such as Nb and Ta.

Also, the heteropoly-acid used has one central atom selected from the group consisting of P, Si, As, Ge, Ti, Ce, Th, Mn, Ni, Te, I, Co, Cr, Fe, Ga, B, V, Pt, Be and Zn. The atomic ratio of the condensation coordinate atom to the central atom in the heteropoly-acid used in this invention typically ranges from about 2.5 to about 12. Further, a polymer of the heteropoly-acid such as a dimer or a trimer of the heteropoly-acid in addition to the monomeric heteropoly-acid can be employed in this invention.

Exemplary heteropoly-acids which can be employed in this invention include 12-molybdophosphoric acid, 5-molybdo-2-phosphoric acid, 12-tungstophosphoric acid, 12-molybdotungstophosphoric acid, 6-molybdo-6-tungstophosphoric acid, 12-molybdovanadophosphoric acid, 11-molybdo-1-vanadophosphoric acid, 12-molybdotungstovanadophosphoric acid, 12-tungstovanadophosphoric acid, 12-molybdoniobophosphoric acid, 12-tungstosilicic acid, 12-molybdosilicic acid, 12-molybdotungstosilicic acid, 12-molybdotungstovanadosilicic acid, 12-tungstoboric acid, 12-molybdoboric acid, 12-molybdotungstoboric acid, 12-molybdovanadoboric acid, 12-molybdotungstovanadoboric and, 9-molybdonickelic acid, 6-molybdocobaltic acid, 6-tungstocobaltic acid, 11-molybdoarsenic acid, 12-tungstoarsenic acid, 12-tungstogermanic acid and 18-tungsto-2-arsenic acid.

The heteropoly-acids used in the process of this invention are employed in the form of an aqueous solution thereof.

The concentration of the heteropoly-acid used is not particularly limited. At higher concentrations of the heteropoly-acid in the aqueous solution the hydration reaction of isobutylene preferably proceeds faster but it is unnecessary to use the heteropoly-acid above its solubility in water. On the other hand, at extremely low concentrations of the heteropoly-acid the rate of reaction is reduced. A suitable concentration of the heteropoly-acid in the hydration reaction which can be employed in this invention typically ranges from about 10% by weight, based on the total amount of water and the heteropoly-acid, to the saturation solubility in water of the heteropoly-acid at the reaction temperature. In the present process, the heteropoly-acid may be previously prepared and added to the hydration reaction or a compound having the central atom and a compound having the condensation coordinate atom are separately added to a reactor to firstly form a heteropoly-acid, and secondly the resulting heteropoly-acid may be contacted with a hydrocarbon mixture comprising isobutylene and n-butene.

It is necessary that the hydration reaction according to the process of this invention is carried out at a temperature of less than 100° C. A preferred temperature ranges from about 30° C. to about 80° C. When the hydration reaction temperature is higher than 100° C., the hydration of n-butene occurs rapidly, the purity of tert-butanol in a product reduces and moreover, formation of oligomers such as the dimer or the trimer of the polymers of isobutylene increases, and sec-butyl tert-butyl ether which becomes an obstacle in the purification of tert-butanol and which tends to produce the dangerous peroxide starts forming. On the other hand, especially when the hydration reaction temperature is less than about 80° C., hardly any hydration of n-butene occurs, and tert-butanol having a high purity can be obtained. Although the hydration reaction reaction according to the process of this invention can be carried less than about 30° C., the rate of reaction decreases disadvantageously.

In this embodiment, 12-molybdophosphoric acid, 12-molybdosilicic acid, 12-tungstosilicic acid and 12-tungstophosphoric acid are preferred of the heteropoly-acids which can be employed in this invention.

The process of this invention is carried out at least at the pressure required to maintain water, isobutylene and n-butene in the form of liquid under the reaction conditions or at a higher pressure. In controlling the pressure, an inert gas such as nitrogen can also be employed.

Further, when an acidic substance including inorganic acids such as sulfuric acid, nitric acid, hydrochloric acid, phosphoric acid, silicic acid; aromatic sulfonic acids such as p-toluenesulfonic acid; and strongly acidic ion-exchange resins is present in the hydration reaction of this invention in a weight ratio of the acidic substance to the heteropoly-acid employed of not more than about 0.01, the excellent selectivity of isobutylene to tert-butanol and the catalytic activity of the heteropoly-acid can be maintained and the stability of the heteropoly-acid can also be improved and as a result, the life of the heteropoly-acid can be prolonged. However, when the amount of such acidic substances employed is too large, the disadvantages originating from each of the acidic substances selected are brought about. For example, in using sulfuric acid, formation of the by-products such as the oligomers of isobutylene and sec-butanol increases and corrosion of the reactor occurs disadvantageously.

According to this invention it is necessary that the remaining hydrocarbons after the selective hydration reaction of isobutylene are removed from the hydration reaction mixture liquid at a temperature of at most 70° C. in order to avoid dehydration of tert-butanol and other side-reactions. In removing the remaining hydrocarbons, for example, the hydration reaction mixture liquid after the hydration reaction separates into two liquid phases under pressure, i.e., an organic liquid phase containing the remaining hydrocarbons and an aqueous liquid phase containing the heteropoly-acid as the catalyst and then the organic liquid phase may be separated from the aqueous liquid phase under pressure or after the phase separation the organic liquid phase may be evaporated. Further, if necessary or if desired, the remaining hydrocarbons dissolved in the aqueous liquid phase may be removed under reduced pressure. Thus, the tert-butanol produced is obtained generally in the form of an aqueous solution thereof. When a tert-butanol aqueous solution of a higher concentration is desired, the aqueous solution is subjected to purification.

It is also necessary that the recovery or purification of tert-butanol from the aqueous liquid phase after separation of the remaining hydrocarbons is conducted at a temperature of at most about 70° C. in order to avoid formation of by-products of tert-butanol. For the recovery or purification of tert-butanol, any method such as flashing, reduced pressure distillation, extraction and salting out can be employed. Of these methods, reduced pressure distillation of any type such as simple distillation, packed tower distillation or plate tower distillation is preferably employed. Since it is unfavorable to leave the tert-butanol produced under heating for a long period of time, the recovery or purification is preferably conducted in a period of time as short as possible.

According to this invention, the aqueous liquid after separation of tert-butanol may be recycled to the hydration reactor. In this case, even if complete recovery of tert-butanol is not conducted, the loss of tert-butanol is advantageously small. In recycling the aqueous liquid, the concentration of water in the hydration reaction mixture can be maintained constant by adding thereto water in an amount corresponding to the amount lost as a tert-butanol aqueous solution from the hydration reaction system.

On the other hand, if a mixture of the remaining hydrocarbons with a content of isobutylene is separated from the hydration reaction mixture liquid, the mixture may also be recycled to the hydration reactor.

In another embodiment of this invention, the selective hydration of isobutylene as described above can be conducted in the presence of tert-butanol in the aqueous liquid phase of a hydration reaction mixture consisting of two liquid phases, i.e., an organic liquid phase and an aqueous liquid phase. In this embodiment, the amount of tert-butanol is adjusted in such a manner that the organic liquid phase contains tert-butanol in the same or almost the same amount as that produced by the hydration of isobutylene, and in addition, contains the fed hydrocarbons and the aqueous liquid phase contains almost all the heteropoly-acid and water in the hydration reaction system. The amount of tert-butanol in the aqueous liquid phase which can be employed in this embodiment typically ranges from about 5 to about 30% by weight based on the total weight of the aqueous liquid phase.

After the hydration reaction the organic liquid phase contains tert-butanol in the same or almost the same amount as that produced by the hydration reaction, a small amount of water and the remaining hydrocarbons and the aqueous liquid phase contains the heteropoly-acid, water, the dissolved hydrocarbons and tert-butanol in an amount corresponding or almost corresponding to that added before the hydration reaction. After separation of the organic liquid phase from the aqueous liquid phase and removal of the remaining hydrocarbons from the organic liquid phase thus separated, a highly concentrated tert-butanol aqueous solution can be obtained.

The aqueous liquid phase can be further used in the selective hydration reaction of isobutylene.

In this embodiment, 12-tungstosilicic acid and 12-tungstophosphoric acid are preferred heteropoly-acids since the amount of tert-butanol which is required to be present in the hydration reaction is advantageously small.

It goes without saying that the amount of tert-butanol present in the hydration reaction system varies depending upon the heteropoly-acid selected, the amount of the heteropoly-acid employed, the reaction temperature chosen and other factors.

In the selective hydration reaction of isobutylene the aqueous liquid phase as such or after partial removal of tert-butanol can be recycled to the hydration reaction.

Further, when the hydration reaction of this invention using tert-butanol is conducted in the presence of an inorganic acid salt, the amount of tert-butanol present in the hydration reaction can be reduced. As described above, according to this invention it is necessary to transfer the same or almost the same amount of tert-butanol as that produced from isobutylene to the organic liquid phase of the reaction mixture liquid. When any inorganic acid salt is not added to the hydration reaction, the distribution coefficient of tert-butanol to the organic liquid phase is small. Thus, it is necessary to increase the concentration of tert-butanol in the aqueous liquid phase of the reaction mixture liquid and as a result, a large amount of tert-butanol is required to be present in the aqueous liquid phase. However, the presence of an inorganic acid salt in the hydration reaction can increase the distribution coefficient of tert-butanol to the organic liquid phase in the hydration reaction mixture and makes possible the recovery of tert-butanol produced from the organic liquid phase and the aqueous liquid phase as well even with comparatively reduced amounts of tert-butanol present in the aqueous liquid phase.

Specific examples of suitable inorganic acid salts include sulfates, bisulfates, nitrates and phosphates. Metal halides are not suitable due their strong corrosion. Appropriate cations which can be employed in this invention include any cations which do not form insoluble salts with the heteropoly-acid of this invention. Spefific examples of these cations include lithium, sodium, magnesium, beryllium, aluminum, nickel, copper, zinc, cobalt, silver, iron, chromium and manganese cations. Potassium salts and ammonium salts which form insoluble heteropoly-acid salts cannot be employed.

When the amount of the inorganic salt is too large, the hydration reaction system becomes three liquid phases or two liquid phases and one solid phase. Thus, the amount of the inorganic salt used in this invention is not critical unless the hydration reaction system becomes three liquid phases or two liquid phases and one solid phase.

The reactors which can be employed in this invention include tank reactors equipped with a stirrer, multiple compartment reactors equipped with a stirrer, externally circulating reactors, bubble cap reactors, packed reactors, wetted-wall reactors, tube reactors.

The process of this invention can be carried out either batchwise, sem-continuously or continuously.

The advantage of this invention will be understood from FIG. 1 illustrating the results of the selective hydration of isobutylene using an aqueous solution of 12-molybdophosphoric acid as an exemplary catalyst in Example 2. More specifically, it is clear that at temperatures of less than 100° C. and preferably less than about 80° C., the effect of the selective hydration of isobutylene becomes distinct, and at the same time the hydration activity of the catalyst at such low temperatures is very high with extremely reduced amounts of by-products such as the dimer and the trimer of isobutylene.

To provide a clearer and better understanding of this invention, reference will now be made to preferred embodiments thereof in connection with the flow diagrams shown in the drawings.

Figure 2:
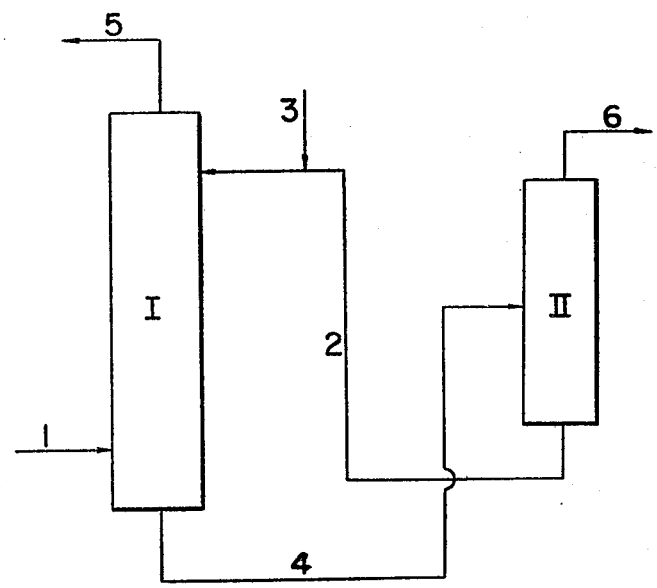
FIG. 2 illustrates the flow diagram of an apparatus of one embodiment of this invention.

In one embodiment illustrated in FIG. 2 which is a continuous reaction system according to the process of this invention, I denotes a reactor and II denotes a distillation column.

To reactor I are supplied a hydrocarbon mixture comprising isobutylene and n-butene through line 1 and at the same time a mixture of a recycling liquid comprising water and a heteropoly-acid from distillation column II through line 2 and additional water through line 3. In reactor I the hydrocarbon mixture is countercurrently contacted with the mixture of the recycling liquid and the additional water with stirring. The remaining hydrocarbon mixture is collected from the top of reactor I through line 5 while an aqueous liquid containing tert-butanol formed and the catalyst is transferred from the bottom of reactor I to distillation column II through line 4. The tert-butanol formed is collected from the top of distillation column II through line 6 while an aqueous liquid comprising the catalyst is recycled from the bottom of distillation column II through line 2 to reactor I together with additional water through line 3 in an amount corresponding to the amount reduced in the reaction and escaped from the reaction system.

Figure 3:
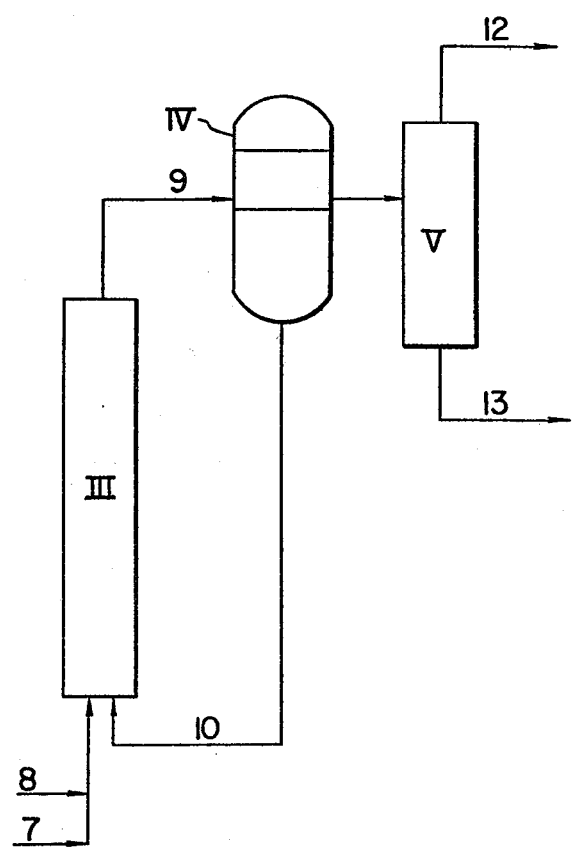
FIG. 3 illustrates the flow diagram of an apparatus of another embodiment of this invention.

In another embodiment illustrated in FIG. 3 which is a continuous reaction system according to the process of this invention, III denotes a reactor; IV decanter; and V an evaporator.

To the bottom of reactor II are fed a hydrocarbon mixture comprising isobutylene and n-butene through line 8, additional water through line 7 and the lower phase in decanter IV comprising water, the catalyst and tert-butanol through line 10. The selective hydration of isobutylene is conducted with stirring in reactor III and the hydration reaction mixture liquid is fed to decanter IV and then the upper phase in decanter IV is transferred to evaporator V through line 11. The remaining hydrocarbon mixture is collected from evaporator V through line 12 by decreasing the pressure of evaporator V to atmospheric pressure or by heating under a pressure. The hydrocarbons thus recovered may be liquified by any conventional method such as cooling with brine or cooling after compression. The remaining portion after removal of the hydrocarbons in evaporator V is a concentrated tert-butanol aqueous solution typically containing about 87 to 92% by weight of tert-butanol which may be further purified by simple distillation. The lower phase in decanter IV which is an aqueous phase is recycled to reactor III through line 10 as such or if necessary, after part of tert-butanol has been distilled off.

The following Examples are given to illustrate the present invention more specifically. However, it should be understood that the invention is in no way limited by these Examples.

In these Examples the analysis of products was conducted as follows;

Using dimethoxyethane as the internal standard substance, a product was diluted with methanol by about 5 times, neutralized with sodium hydroxide and subjected to gas chromatography under the following conditions:

| Apparatus | Hitachi Model 163 |
|---|---|
| Packing Agent | Chromosorb 101, made by Wako Junyaku Co., Ltd. |
| Column Length | 2 m |
| Column Temperature | 140° C. |
| Injection Temperature | 160° C. |
| Carrier | Helium 50 cc/min |

EXAMPLE 1

Into a 300 ml stainless steel autoclave were charged 10 g of isobutylene, 10 g of 1-butene, 50 g of a heteropoly-acid as set forth in Table 1 and 100 g of water, and the mixture was stirred at 60° C. at a pressure of 8.5 atms for one hour. The results are shown in Table 1.

In each case, formation of sec-butanol was not detected, and 1-butene was found unreacted. Further, isobutylene polymers such as diisobutylene were not detected.

TABLE 1

| Run No. | Heteropoly-acid | Atomic Ratio Concentration Coordinate atom | : Central atom | Conversion of Tert-isobutylene (%) | Selectivity of Isobutylene to Tert-butanol (%) |
|---|---|---|---|---|---|
| 1 | 12-Molybdophosphoric acid | 12(Mo) | 1(P) | 89 | 100 |
| 2 | 12-Tungstophosphoric acid | 12(W) | 1(P) | 77 | 100 |
| 3 | 12-Tungstosilicic acid | 12(W) | 1(Si) | 79 | 100 |
| 4 | 12-Molybdosilicic acid | 12(Mo) | 1(Si) | 63 | 100 |
| 5 | 12-Tungstoboric acid | 12(W) | 1(B) | 61 | 100 |
| 6 | 12-Tungstoarsenic acid | 12(W) | 1(As) | 43 | 100 |
| 7 | 6-Molybdo-6-tungstophosphoric acid | [6(M) + 6(W)] | 1(P) | 86 | 100 |
| 8 | 11-Molybdo-1-vanadophosphoric acid | [11(Mo) + 1(V)] | 1(P) | 81 | 100 |

TABLE 1-continued

| Run No. | Heteropoly-acid | Atomic Ratio (Concentration Coordinate atom : Central atom) | | Conversion of Tert-isobutylene (%) | Selectivity of Isobutylene to Tert-butanol (%) |
|---|---|---|---|---|---|
| 9 | 5-Molybdo-2-phosphoric acid | 5(Mo) | 2(P) | 89 | 100 |
| 10 | 9-Molybdonickelic acid | 9(Mo) | 1(Ni) | 59 | 100 |
| 11 | 6-Tungstocobaltic acid | 6(W) | 1(Co) | 60 | 100 |
| 12 | 12-Tungstogermanic acid | 12(W) | 1(Ge) | 84 | 100 |

EXAMPLE 2

Into a 300 ml stainless steel autoclave were charged 10 g of isobutylene, 10 g of 1-butene, 50 g of 12-molybdophosphoric acid having an atomic ratio of P to Mo of 1 to 12 and 100 g of water, and the mixture was stirred under the conditions as set forth in Table 2. The results are shown in Table and in FIG. 1.

TABLE 2

| Run No. | Temperature (°C.) | Pressure (atms.) | Period of Time of Stirring (hour) | Concentration of Tert-butanol Produced (weight %) | Weight Ratio of Sec-butanol to Tert-butanol | Weight Ratio of Diisobutylene to Tert-butanol |
|---|---|---|---|---|---|---|
| 1 | 60 | 8.5 | 1 | 10.1 | 0 | 0 |
| 2 | 80 | 14 | 1 | 9.1 | 0.001 | 0 |
| 3 | 100 | 19 | 1 | 7.8 | 0.017 | 0 |
| 4 | 120 | 28 | 0.5 | 6.5 | 0.045 | 0.015 |
| 5 | 130 | 33 | 0.5 | 5.7 | 0.085 | 0.038 |
| 6 | 150 | 45 | 0.5 | 3.5 | 0.37 | 0.27 |

EXAMPLE 3

Into a 300 ml stainless steel autoclave were charged 20 g of a hydrocarbon mixture having a composition as set forth in Table 3 (so-called "Spent B-B Fraction"), 50 g of 12-tungstophosphoric acid having an atomic ratio of P to W of 1 to 12 and 100 g of water, and the mixture was stirred at 60° C. at a pressure of 8.5 atms for one hour. As a result, only the isobutylene was reacted to form its hydrated compound, i.e., tert-butanol. The results are as follows:

| | |
|---|---|
| Conversion of isobutylene | 77% |
| Selectivity of isobutylene to tert-butanol | 100 |
| Formation of sec-butanol | Not detected |
| Formation of the dimer, trimer and polymers | Not detected |

TABLE 3

| Hydrocarbon | Weight % |
|---|---|
| Isobutylene | 47.15 |
| 1-Butene | 26.16 |
| 2-Butene | 14.32 |
| Butanes | 11.75 |
| Propane | 0.10 |
| Pentanes | 0.13 |
| Butadiene | 0.39 |

COMPARATIVE EXAMPLE

Into a 300 ml pressure-resistant glass autoclave were charged 10 g of isobutylene, 10 g of 1-butene, 50 g of sulfuric acid and 50 g of water, and the mixture was stirred at 60° C. at a pressure of 8.5 atms for one hour. As a result, isobutylene was hydrated to form tert-butanol with the conversion of 90% and the selectivity to tert-butanol of 92%. At the same time, diisobutylene and the trimer of isobutylene were produced at a yield of 2% and 6%, respectively, and 1-butene was hydrated to form sec-butanol at a yield of 4%.

EXAMPLE 4

Into a 300 ml stainless steel autoclave were charged 10 g of isobutylene, 10 g of 1-butene, 50 g of 12-tungstophosphoric acid having an atomic ratio of P to W of 1 to 12, and the mixture was stirred at 60° C. at a pressure of 8.5 atms for one hour, and left to stand under cooling to 20° C. Then the organic liquid phase was separated from the aqueous phase containing tert-butanol and the catalyst and degassed at 40° C./300 mmHg to obtain 2.3 g (recovery rate:23%) of isobutylene from the remaining hydrocarbon mixture. On the other hand, the aqueous phase was supplied to the bottom of a distillation column packed with "Naniwa Pack" (stainless steel spiral wires having a length of 3 mm; manufactured by Naniwa Tokushu Kanaami Co., Ltd.) at a packed height of 10 cm and subjected to distillation at a temperature of 40° C. to 60° C. under a reduced pressure of 150 mmHg to give 12.4 g of a 80% tert-butanol aqueous solution at a yield of tert-butanol of 75%. At this time, formation of sec-butanol was not observed.

Further, to the remaining aqueous solution containing the catalyst were added 2.5 g of water, 10 g of isobutylene and 10 g of 1-butene, and the mixture was stirred at 60° C. under a pressure of 8.5 atms for one hour to give tert-butanol at a yield of 77% and a selectivity of 100%.

EXAMPLE 5

Into a 300 ml stainless steel autoclave were charged 20 g of the same hydrocarbon mixture as in Example 3, 50 g of 12-molybdophosphoric acid having an atomic ratio of P to Mo of 1 to 12 and 100 g of water, and the mixture was stirred at 60° C. at a pressure of 8.5 atms for 2 hours and the organic liquid phase of the hydrocarbon mixture was vaporized to obtain 0.4 g of isobutylene. On the other hand, the aqueous phase was subjected to distillation in the same manner as in Example 4 to give 15.9 g of a 80% tert-butanol aqueous solution at a yield of tert-butanol of 96% and a selectivity to tert-butanol of 100%. At this time, formation of sec-butanol was not observed.

Further, to the remaining aqueous solution were added 3.5 g of water, 10 g of isobutylene and 10 g of 1-butene, and the mixture was stirred at 60° C. at a pressure of 8.5 atms for 2 hours to give tert-butanol at a yield of 96% and a selectivity of 100% without forming sec-butanol, the dimer, trimer and polymers of isobutylene.

EXAMPLE 6

The apparatus as shown in FIG. 2 was employed in this Example. Reactor I employed had a 120 ml reaction zone and two separation zones, one at the upper portion of the reaction zone and the other at the lower portion of the reaction zone and the reaction zone was divided into 7 compartments and each compartment was stirred with a flat stirring paddle. The same so-called spent B-B fraction as in Example 3 was fed at a rate of 50 ml per hour to the lowest compartment of reactor I through line 1 and at the same time a recycling liquid containing water and 12-tungstophosphoric acid having an atomic ratio of P to W of 1 to 12 in a weight ratio of 1 to 2 coming from distillation column II through line 2 was fed at a rate of 442 g per hour to the highest compartment of reactor I. In reactor I the so-called spent B-B fraction and the mixture of the recycling liquid and the additional water was countercurrently contacted with each other at 70° C. and 10 atms. The remaining hydrocarbon mixture was collected from the upper separation zone of reactor I through line 5 while an aqueous solution containing tert-butanol formed and the 12-tungstophosphoric acid was transferred from the lower separation zone of reactor I through line 4 to distillation column II. Then, the tert-butanol formed was collected by distillation from the top of distillation column II through line 6 and an aqueous solution containing the 12-tungstophosphoric acid was recycled from the bottom of distillation column II through line 2 to the highest compartment of reactor I together with additional water through line 3 in an amount corresponding to the amount reduced in the reaction and escaped from the reaction system. The conversion of isobutylene was 95.4% and the amount of isobutylene polymers such as diisobutylene formed was at most 1,000 ppm based on the weight of tert-butanol produced and the selectivity of isobutylene to tert-butanol was quantitative.

EXAMPLE 7

The procedure of Example 6 were repeated except that a recycling liquid containing 49.7% by weight of water, 50.5% by weight of 12-molybdophosphoric acid having an atomic ratio of P to Mo of 1 to 12 and 0.3% by weight of phosphoric acid was fed at a rate of 450 g per hour to the highest compartment of reactor I. The conversion of isobutylene was 96.5%. After the hydration reaction was continued further for 1,000 hours, the conversion of isobutylene was 96.3%.

EXAMPLE 8

Into a 300 ml stainless steel autoclave were charged 11.2 g of isobutylene, 16.8 g of 1-butene, 136 g of 12-tungstosilicic acid having an atomic ratio of Si to W of 1 to 12, 136 g of water and 41.0 g of tert-butanol, and the mixture was stirred at 60° C. at a pressure of 8.5 atms for 2 hours. The conversion of isobutylene was 83.1%. Then the reaction mixture was left to stand and separated into two phases, followed by evaporation of the remaining hydrocarbon mixture in the upper phase at atmospheric pressure to give 13.5 g of a concentrated tert-butanol aqueous solution containing 90% by weight of tert-butanol and 9.0% by weight of water. The lower phase contained 40.8 g of tert-butanol. The selectivity of isobutylene to tert-butanol was almost quantitative.

EXAMPLE 9

The procedure of Example 8 were repeated except that the amount of the tert-butanol in the feed was changed to 38.6 g. The conversion of isobutylene was 86.6%. After the reaction, the reaction mixture was left to stand and separated into two phases, followed by evaporation of the remaining hydrocarbon mixture in the upper phase at atmospheric pressure to give 13.1 g of a concentrated tert-butanol aqueous solution containing 90.1% by weight of tert-butanol and 8.9% by weight of water. The lower phase contained 39.6 g of tert-butanol. The selectivity of isobutylene to tert-butanol was almost quantitative.

EXAMPLE 10

Into a 300 ml stainless steel autoclave were charged 8.0 g of isobutylene, 12.0 g of 1-butene, 97 g of 12-molybdophosphoric acid having an atomic ratio of P to Mo of 1 to 12, 97 g of water and 56 g of tert-butanol, and the mixture was stirred at 60° C. at a pressure of 8.5 atms for 3 hours. The conversion of isobutylene was 81.4%. Then the reaction mixture was left to stand and separated into two phases, followed by evaporation of the remaining hydrocarbon mixture in the upper phase at atmospheric pressure to give 9.4 g of a concentrated tert-butanol aqueous solution containing 90.1% by weight of tert-butanol and 8.8% by weight of water. The lower phase contained 55.8% by weight of tert-butanol. The selectivity of isobutylene to tert-butanol was almost quantitative.

EXAMPLE 11

Into a 300 ml stainless steel autoclave were charged 8.0 g of isobutylene, 12.0 g of 1-butene, 200 g of 12-tungstophosphoric acid having an atomic ratio of P to W of 1 to 12, 100 g of water and 65.0 g of tert-butanol, and the mixture was stirred at 40° C. at a pressure of 6.0 atms for 3 hours. The conversion of isobutylene was 83.0%. The reaction mixture thus obtained was left to stand and separated into two phases, followed by evaporation of the remaining hydrocarbon mixture in the upper phase at atmospheric pressure to give 9.1 g of a concentrated tert-butanol aqueous solution containing 90.2% by weight of tert-butanol and 8.8% by weight of water. The lower phase contained 65.5 g of tert-butanol. The selectivity of isobutylene to tert-butanol was almost quantitative.

EXAMPLE 12

The apparatus as shown in FIG. 3 was employed in this Example.

A so-called spent B-B fraction containing 40.0% by weight of isobutylene, 31.2% by weight of 1-butene, 17.32% by weight of 2-butene, 13.75% by weight of butane, 0.1% by weight of propane, 0.1% by weight of pentane and 0.4% by weight of butadiene was supplied at a rate of 200 g per hour to the bottom of 10 l of reactor III through line 8 and at the same time a recycling liquid having a composition of 17.2% by weight of tert-butanol, 27.6% by weight of water and 55.2% by weight of 12-tungstosilicic acid having an atomic ratio of Si to W of 1 to 12 was fed to the bottom of reactor III from decanter IV through line 10 and the mixture was throughly stirred at 40° C. at a pressure of 6.0 atms in reactor III. The reaction mixture solution was transferred to decanter IV where the temperature and the pressure were maintained at 40° C. and 6.0 atms, respectively and the reaction mixture solution was separated into two phases. The upper phase in decanter IV was fed at a rate of 233.4 g per hour to evaporator V where the temperature and the pressure were maintained at 30° C. and atmospheric pressure and the remaining hydrocarbon mixture was recovered at a rate of 128 g per hour from the top of evaporator V through line 12. On the other hand, from the bottom of evaporator V was collected a concentrated tert-butanol aqueous solution at a rate of 105 g per hour through line 13. The lower phase in decanter IV was recycled to reactor III through line 10 while water was fed to the bottom of reactor III through line 7 at a rate of 32.5 g per hour which corresponded to the amount reduced in the reaction and escaped from the reaction system. The apparatus employed was of stainless steel (SUS 27).

EXAMPLE 13

Into a 300 ml stainless steel (SUS 27) autoclave were charged 12.8 g of isobutylene, 19.2 g of 1-butene, 120 g of 12-tungstosilicic acid having an atomic ratio of Si to W of 1 to 12, 32 g of lithium sulfate, 12.0 g of tert-butanol and 160 g water, and the mixture was stirred at 60° C. at a pressure of 8.5 atms for 7 hours. The conversion of isobutylene was 77.8%. The reaction mixture thus obtained was left stand and separated into two phases, followed by evaporation of the remaining hydrocarbon mixture in the upper phase at atmospheric pressure to give 14.7 g of a concentrated tert-butanol aqueous solution containing 88.9% by weight of tert-butanol and 10.1% by weight of water. On the other hand, from the lower phase were recovered 12.1 g of tert-butanol. The selectivity of isobutylene to tert-butanol was almost quantitative.

EXAMPLE 14

The procedures of Example 13 were repeated except that an inorganic acid salt as set forth in Table 4 was employed instead of the lithium sulfate and a period of reaction time as set forth in Table 4 was employed. The selectivity of isobutylene to tert-butanol was almost quantitative. The results are shown in Table 4.

TABLE 4

| Run No. | Inorganic Acid Salt | (g) | Period of Reaction Time (hours) | Conversion of Isobutylene (%) | Amount of Tert-butanol in Upper Phase [weight (g)] |
|---|---|---|---|---|---|
| 1 | Na$_2$SO$_4$ | 32 | 5 | 52 | 8.7 |
| 2 | NaHSO$_4$ | 32 | 2 | 80 | 14.5 |
|   | AgNO$_3$ | 1 |   |   |   |
| 3 | NiSO$_4$ | 32 | 5 | 30 | 8.1 |
| 4 | ZnSO$_4$ | 32 | 5 | 62 | 11.0 |
| 5 | Al$_2$(SO$_4$)$_3$ | 32 | 5 | 60 | 10.5 |
| 6 | CuSO$_4$ | 32 | 5 | 57 | 9.9 |
| 7 | MnSO$_4$ | 32 | 5 | 35 | 7.1 |
| 8 | CoSO$_4$ | 32 | 5 | 33 | 7.9 |
| 9 | MgSO$_4$ | 32 | 5 | 48 | 8.5 |

EXAMPLE 15

The apparatus as shown in FIG. 3 was employed in this Example.

The same hydrocarbon mixture as in Example 12 was fed at a rate of 600 g per hour to the bottom of reactor III through line 8 at the same time a mixture of a recycling liquid having a composition of 54.1% by weight of water, 20.3% by weight of 12-tungstosilicic acid having an atomic ratio of Si to W of 1 to 12, 21.7% by weight of lithium sulfate and 3.9% by weight of tert-butanol from decanter IV through line 10 and additional water through line 7 was fed at a rate of 2955 g per hour to the bottom of reactor III. In reactor III the mixture was stirred at 50° C. at a pressure of 7.0 atms and the reaction mixture solution was transferred to decantor IV whose temperature and pressure was maintained at 50° C. and 7.0 atms. The upper phase in decanter IV was fed to evaporator V whose temperature and pressure were maintained at 30° C. and atmospheric pressure, and the remaining hydrocarbon mixture was recovered at a rate of 385 g per hour from the top of evaporator V through line 12 while a concentrated tert-butanol aqueous solution containing 89% by weight of tert-butanol and 10% by weight of water was recovered at a rate of 318 g per hour from the bottom of evaporator V through line 13. The lower phase in decanter IV was recycled to the bottom of reactor III through line 10 and water was fed to the bottom of reactor III from line 7 at a rate of 100 g per hour which corresponded to the amount reduced in the reaction and escaped from the reaction system. The apparatus employed was of stainless steel (SUS 27).

What is claimed is:

1. A process for producing tert-butanol by selective hydration of isobutylene which comprises contacting a hydrocarbon mixture comprising isobutylene and n-butene with an aqueous solution containing a heteropoly-acid having at least one condensation coordinate atom selected from the group consisting of Mo, W and V at a temperature of less than 100° C.

2. The process as claimed in claim 1, wherein the process is carried out at a temperature in the range from about 30° C. to about 80° C.

3. The process as claimed in claim 1, wherein the process is carried out at least at a pressure where the aqueous phase and the hydrocarbon mixture are in a liquid state or at a higher pressure.

4. The process as claimed in claim 1, wherein the process is carried out at a concentration of the heteropoly-acid in the range from about 10% by weight based on the total amount of water and the heteropoly-acid upto the saturation concentration in water at the reaction temperature.

5. The process as claimed in claim 1, wherein the heteropoly-acid has one central atom selected from the group consisting of P, Si, As, Ge, Ti, Ce, Th, Mn, Ni, Te, I, Co, Cr, Fe, Ga, B, V, Pt, Be and Zn in an atomic ratio of the condensation coordinate atom to the central atom of about 2.5 to about 12.

6. The process as claimed in claim 5, wherein the heteropoly-acid is selected from the group consisting of 12-molybdophosphoric acid, 5-molybdo-2-phosphoric acid, 12-tungstophosphoric acid, 12-molybdotungstophosphoric acid, 6-molybdo-6-tungstophosphoric acid, 12-molybdovanadophosphoric acid, 11-molybdo-1-vanadophosphoric acid, 12-molybdotungstovanadophosphoric acid, 12-tungstovanadophosphoric acid, 12-molybdoniobophosphoric acid, 12-tungstosilicic acid, 12-molybdosilicic acid, 12-molybdotungstosilicic acid, 12-molybdotungstovanadosilicic acid, 12-tungstoboric acid, 12-molybdoboric acid, 12-molybdotungstoboric acid, 12-molybdovanadoboric acid, 12-molybdotungstovanadoboric acid, 9-molybdonickelic acid, 6-molybdocobaltic acid, 6-tungstocobaltic acid, 12-tungstogermanic acid, 11-molybdoarsenic acid, 12-tungstoarsenic acid and 18-tungsto-2-arsenic acid.

7. The process as claimed in claim 6, wherein the heteropoly-acid is 12-molybdophosphoric acid.

8. The process as claimed in claim 6, wherein the heteropoly-acid is 12-molybdosilicic acid.

9. The process as claimed in claim 6, wherein the heteropoly-acid is 12-tungstosilicic acid.

10. The process as claimed in claim 6, wherein the heteropoly-acid is 12-tungstophosphoric acid.

11. The process as claimed in claim 1, wherein the process is carried out in the presence of an additional acidic substance selected from the group consisting of inorganic acids, aromatic sulfonic acids and strongly acidic ion-exchange resins, the weight ratio of said additional acidic substance to said heteropoly-acid being not more than about 0.01.

12. The process as claimed in claim 1, wherein the process is carried out continuously.

13. The process as claimed in claim 11, wherein the additional acidic substance is an inorganic acid selected from the group consisting of phosphoric acid, sulfuric acid, hydrochloric acid, nitric acid and silicic acid.

14. The process as claimed in claim 1, wherein the process includes separating unreacted hydrocarbons from the reaction mixture liquid at a temperature of not more than about 70° C.

15. The process as claimed in claim 14, wherein the process includes separating the tert-butanol formed from the aqueous phase at a temperature of not more than about 70° C. after removal of unreacted hydrocarbons from the reaction mixture liquid.

16. The process as claimed in claim 1, wherein the process is conducted in the presence of tert-butanol.

17. The process as claimed in claim 16, wherein the process is carried out with two liquid phases, an organic liquid phase and an aqueous liquid phase, where the organic liquid phase contains tert-butanol in an amount which corresponds approximately or corresponds to the amount produced by the hydration of isobutylene.

18. The process as claimed in claim 16, wherein the process is carried out at an amount of tert-butanol in the aqueous liquid phase in the range of from about 5 to about 30% by weight based on the total weight of the aqueous liquid phase.

19. The process as claimed in claim 16, wherein the heteropoly-acid is 12-tungstosilicic acid.

20. The process as claimed in claim 16, wherein the heteropoly-acid is 12-tungstophosphoric acid.

21. The process as claimed in claim 17, wherein the process is carried out in the presence of an inorganic salt.

22. The process as claimed in claim 21, wherein the inorganic salt is selected from the group consisting of sulfates, bisulfates and phosphates of lithium, sodium, magnesium, beryllium, aluminum, nickel, copper, zinc, cobalt, silver, iron, chromium and manganese.

23. The process as claimed in claim 17, wherein the process is carried out continuously.

24. The process as claimed in claim 23, wherein the process includes partially or totally recycling the aqueous liquid phase as such or after partial removal of tert-butanol.

* * * * *

UNITED STATES PATENT AND TRADEMARK OFFICE
CERTIFICATE OF CORRECTION

PATENT NO. : 4,236,034
DATED : November 25, 1980
INVENTOR(S) : Atsushi Aoshima et al.

It is certified that error appears in the above—identified patent and that said Letters Patent is hereby corrected as shown below:

1st page, under "Foreign Application Priority Data" change "53/683267" to --53/68326--.

Signed and Sealed this

Fourteenth Day of April 1981

[SEAL]

*Attest:*

RENE D. TEGTMEYER

*Attesting Officer*     *Acting Commissioner of Patents and Trademarks*